(12) United States Patent
Impellizzeri

(10) Patent No.: US 8,951,291 B2
(45) Date of Patent: Feb. 10, 2015

(54) SELF-LOCKING OSTEOSYNTHESIS DEVICE

(75) Inventor: Frédéric Impellizzeri, Salon de Provence (FR)

(73) Assignee: Biotech International, Salon de Provence (FR)

( * ) Notice: Subject to any disclaimer, the term of this patent is extended or adjusted under 35 U.S.C. 154(b) by 791 days.

(21) Appl. No.: 12/788,835

(22) Filed: May 27, 2010

(65) Prior Publication Data

US 2010/0234847 A1    Sep. 16, 2010

Related U.S. Application Data

(63) Continuation of application No. 10/530,683, filed as application No. PCT/FR03/02968 on Oct. 8, 2003, now abandoned.

(30) Foreign Application Priority Data

Oct. 9, 2002    (FR) ...................................... 02 12534

(51) Int. Cl.
```
A61B 17/58      (2006.01)
A61B 17/80      (2006.01)
A61B 17/86      (2006.01)
```
(52) U.S. Cl.
CPC ......... *A61B 17/8057* (2013.01); *A61B 17/8085* (2013.01); *A61B 17/8605* (2013.01); *A61B 17/864* (2013.01)
USPC ......................................... 606/291; 606/290

(58) Field of Classification Search
USPC ............................ 606/280, 70–71, 281–299
See application file for complete search history.

(56) References Cited

U.S. PATENT DOCUMENTS

| | | | |
|---|---|---|---|
| 3,596,656 A * | 8/1971 | Kaute ............................. | 606/65 |
| 4,338,926 A * | 7/1982 | Kummer et al. ................ | 606/70 |
| 5,395,371 A * | 3/1995 | Miller et al. ................... | 606/287 |
| 5,578,034 A * | 11/1996 | Estes .............................. | 606/281 |
| 6,004,323 A * | 12/1999 | Park et al. ...................... | 606/246 |
| 6,206,881 B1 * | 3/2001 | Frigg et al. .................... | 606/291 |
| 6,322,562 B1 * | 11/2001 | Wolter ............................ | 606/62 |
| 6,955,677 B2 | 10/2005 | Dahners | |
| 7,641,676 B2 | 1/2010 | Mathieu et al. | |

FOREIGN PATENT DOCUMENTS

| | | |
|---|---|---|
| DE | 196 29 011 A1 | 7/1996 |
| EP | 0 345 133 | 12/1989 |
| FR | 2 794 963 | 12/2000 |
| WO | WO 00/66012 | 11/2000 |
| WO | WO 2009/149057 A1 | 12/2009 |

\* cited by examiner

*Primary Examiner* — Mary Hoffman
(74) *Attorney, Agent, or Firm* — Jackson Walker, LLP

(57) ABSTRACT

The self-locking osteosynthesis device includes a plate equipped with holes for the passage of fixation screws. The invention is characterized in that, at least in the areas defining the screw holes, the aforementioned plate is made from a material having mechanical properties such that the periphery of the holes can be self-tapped by means of tapping screws which can be used to fix the plate.

29 Claims, 5 Drawing Sheets

SELF-LOCKING OSTEOSYNTHESIS DEVICE

This is a continuation patent application that claims priority from and incorporates herein by reference, U.S. patent application Ser. No. 10/530,683, filed Sep. 2, 2005 now abandoned, which is a US National Phase application of PCT International Application No. PCT/FR03/02968, filed on Oct. 8, 2003.

FIELD OF THE INVENTION

The invention relates to a self-locking osteosynthesis or osteotomy device of the type comprising a plate having an appropriate shape designed to be affixed on bone fragments using a screw to ensure their coaptation.

BACKGROUND OF THE INVENTION

The coaptation of the bone fragments using plates of titanium or another material and screws in order to create an osteosynthesis is a common operation in bone surgery, for example, orthopedic surgery.

In order to obtain a good result, it is necessary that the plates or implants are screwed together permanently to the bone fragments assembled from the implants. It is thus a requirement that the screws can not unscrew and move back, to prevent any displacement of the implants relative to the bone fragments.

On the other hand, it would often be desirable to be able to choose the orientation of the screws relative to the plates and as a function of the positioning and the shape of the fragments to be assembled, which can improve the quality of the assembly.

In order to prevent the screws from unscrewing and moving back, it has been proposed (EP0,345,133, FR-2,794,963) to house the locking instruments at the input of the screw holes into the plates, in order to eliminate any possibility of axial movement of the screws, after they are tightened in the bony material. For example, it is provided in the document EP-0,345,133, to use check screws that are outside-threaded and work together with a complementary threading arranged at the input of the holes of the screws that equip the plates, in a manner so that the head of the screws is wedged against a check screw and that the check screws can not move axially relative to the plates, this locking thus ensuring the permanent support of the plate on the bone fragments.

The devices proposed by several manufacturers represent at this time the solutions that are most certain in terms of locking. However, these relatively complex devices require the use of plates having a relatively sizeable thickness that is totally incompatible with a usage for operations on the bones of the hand or foot, for which the thickness of the plates must be as reduced as possible, taking into account the small size of the bones involved.

In the document EP-0.345.133, a device is again shown for connecting two elements such as an implant and a bone, according to which the implant comprises screw holes with axes oriented at an angle to each other, in a manner so that the screws going through these holes have orientations that are rigorously imposed by the direction of these axes. A device of this type can only be planned for the reduction of identical fractures, because otherwise it would be necessary to provide as many plate models as possible cases of fractures, which is practically impossible; in fact, it does not offer any possibility to choose the orientation of the screws as a function of the problems encountered in orthopedic surgery.

In the document WO-00/66012, a plate is described for osteosynthesis that can be locked, according to which the screws and the screw holes provided in the plate are equipped, respectively, with a locking threading and a sensible meshing profile allowing the introduction of the screws into the plate in an angled manner. The practical creation of a device of this type would be difficult and it seems its effectiveness has not been established.

In a general manner, in the field of osteosynthesis of small bones requiring the use of plates having small dimensions, the devices that are currently available on the market do not make possible an angular clearance between the screws and the plate, so that the screws thus have to be positioned perpendicularly to the plate. However, in certain cases, it would be desirable to be able to have one or more screws at an angle in order to use one or more of the better quality bones for tightening the screws.

BRIEF SUMMARY OF THE INVENTION

The invention has the purpose of correcting the shortcomings mentioned above for osteosynthetic systems using plates and screws, notably because of the fact that the existing devices for serious orthopedics (treatment of serious traumatisms) can not be transposed to hand and foot surgery in which the dimension of the plates that can be used becomes considerably reduced.

According to the invention, this purpose is achieved using an osteosynthesis comprising a plate which is equipped with holes for the passage of screws for fixation of this plate onto a bone support. This device is notable in that the osteosynthesis plate is made, at least in the zones that define the screw holes, of a material that has mechanical properties to allow self-tapping of the periphery of the holes with the tapping screws used to fix the plate.

According to another characteristic arrangement, the osteosynthesis plate is made of a composite plate with hole peripheries comprised of inserts made of a plastic biocompatible material, and inserted into the holes in the remaining part of the plate which is made of metal.

According to another characteristic arrangement, the hole peripheries are comprised of inserts made of polyether ether ketone (PEEK), and the remaining part of the plate is made of titanium.

According to another characteristic arrangement, the head of the screws has a conical thread tapping mechanism.

By these characteristic arrangements above, the self-locking head of the screws drills its own helicoid receiving groove in the periphery of the holes in which they are engaged, in a manner so that the screws are then automatically locked in the plate when their head is tightened into its housing.

On the other hand, the osteosynthesis plate according to the invention allows a selective angulation of the screws relative to the axis of the holes of the plate, as a function of the requirements.

In addition to obtaining the results mentioned above that are very much of interest, the osteosynthesis device according to the invention provides several advantages:

- it has a simple design so that it can be made in an economical manner;
- it is easy to implement;
- it is very reliable in its usage;
- it can be used to ensure the locking of fixation screws of osteosynthesis plates having small sizes, which is not allowed by the systems currently proposed on the market.

This osteosynthesis device thus meets perfectly the expectations of surgeons in terms of ease of implementation and reliability of usage.

BRIEF DESCRIPTION OF THE DRAWINGS

The above purposes, characteristics, and advantages, and still others, emerge better from the description that follows and the attached drawings.

DETAILED DESCRIPTION OF THE INVENTION

Reference is made to the drawings in order to describe an embodiment example that is of interest, though in no way restrictive, of the self-locking osteosynthesis device according to the invention.

This device comprises a plate 1 equipped with passage holes 2 and fixation screws 3.

According to the invention, the plate 1 is made, at least in the defining zones of the passage holes 2 of the screws 3, of a material 4 that has the mechanical properties that allow a self-locking of the periphery of these holes using tapping screws for the fixation of the plate on the bone material.

Figure 1:
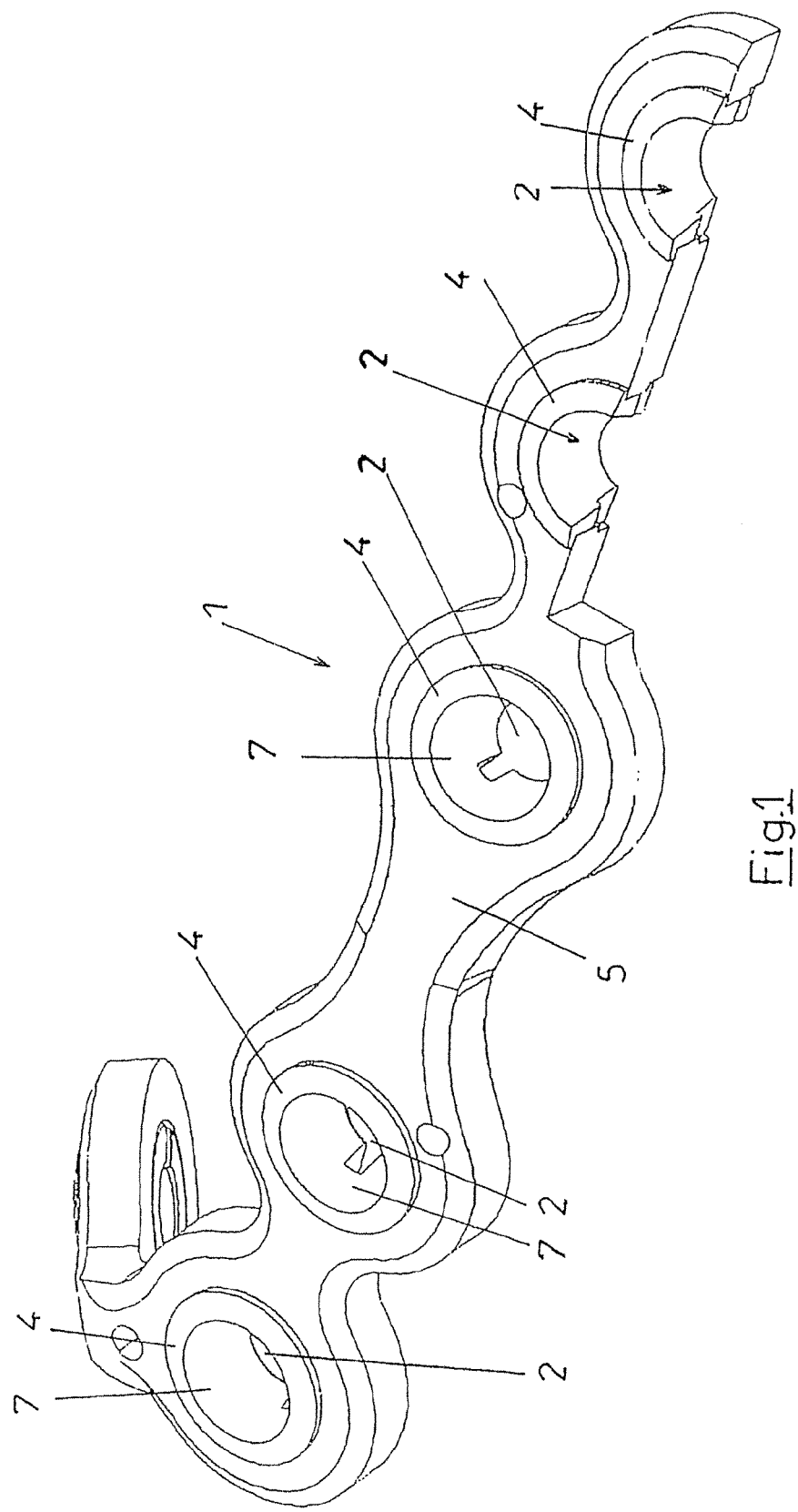
FIG. 1 is a perspective view, with a partial excerpt, of an osteosynthesis plate according to the invention, with a configuration given solely as an example.
Figure 2:
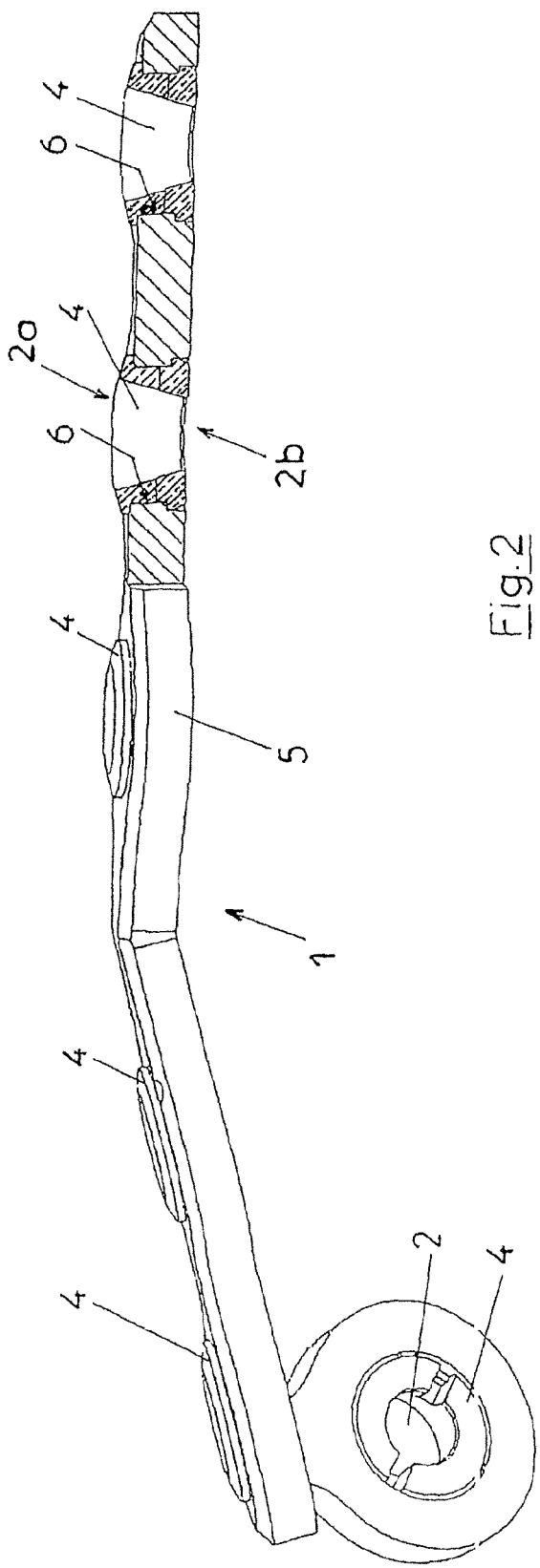
FIG. 2 is a partial side elevation and sectional view of FIG. 1.
Figure 3:
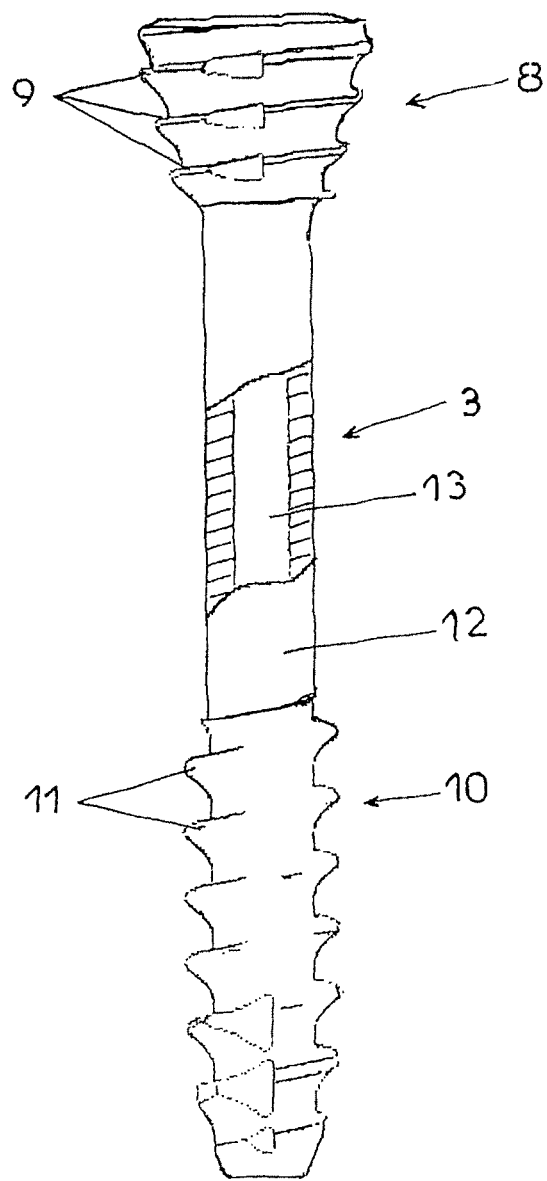
FIG. 3 is an elevation view, with a partial axial section and enlarged scale, of a conical screw head that can be used to implement the invention.
Figure 4:
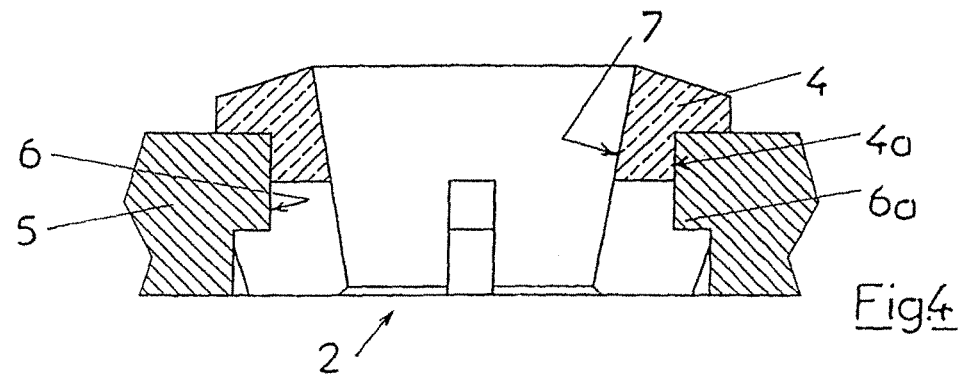
FIG. 4 is a detail sectional view showing, in an axial section, an insert implanted into an osteosynthesis plate for reception of a tapping screw.
Figure 5:
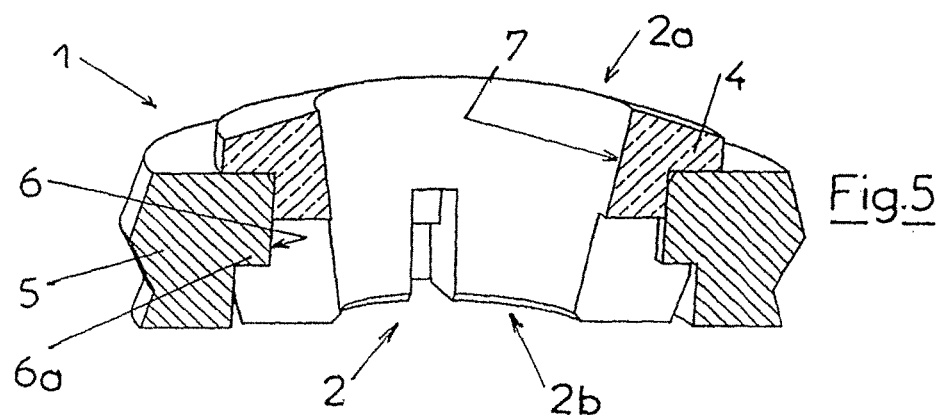
FIG. 5 is a section and perspective view of this insert.
Figure 6:
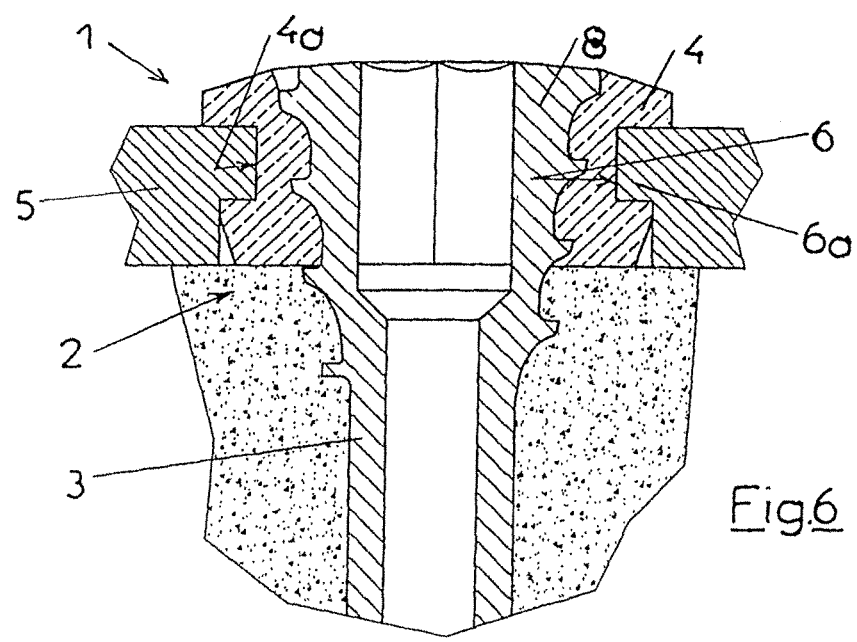
FIG. 6 is a sectional view showing a tapping screw tightened into this insert and into a bone fragment.

The plate 1 can have any shape designed for the cases to be treated with reduction of fractures or restorative surgery; the shape shown in FIG. 1 is thus only a possible example of the shape, and the same applies for the placement of the holes 2 in the plate.

In a preferred manner, the plate 1 is made up of a composite plate whose peripheries 4 of the holes 2 are made of a plastic biocompatible material, the remaining part or surface 5 of the plate being made of metal.

The peripheries 4 of the holes 2 can be made of a high-performance thermoplastic polymer. In a preferred and advantageous manner, the peripheries 4 of the holes 2 are made of polyether ether ketone (PEEK) that has very high mechanical properties and can be machined, like a metal.

The remaining part or surface 5 of the plates 1 can be made of stainless steel, and in a preferred and advantageous manner, it is made of titanium.

The solid fixation of the inserts made from the peripheries 4 of the holes 2 in the holes 6 arranged in the plate having a metal base 5 can be made by a technique of molding from a casting having the advantage of ensuring an intimate contact between the two materials.

However, in a preferred manner, the implementation of the inserts with PEEK 4 into the holes 6 of the metal plate 5 is done by means of a mechanical assembly. The inserts made of PEEK 4 are engaged, by deformation and pressure in the holes of the metal plate and are then held in these holes. For example, the inserts 4 can comprise a peripheral groove 4a in which an upper edge 6a of the holes 6 of the plate 1 come to engage, while the inserts are pushed into the holes. When the screws 3 are screwed in, the inserts 4 deform and are compressed between the edges of the holes 6 of the metal plate 5, which contributes to the solidity of the anchorage of these inserts in the metal plate.

A mechanism is provided to prevent any possibility of rotation of the inserts 4 in the holes 6 of the plate 5 when the screws are screwed into these inserts. This mechanism can, for example, be comprised of one or more grooves arranged in the inside cylindrical surface of the holes 6 of the plate 5, in parallel to the axis of the holes.

Using the mechanisms described above, the inserts 4 are solidly connected to the plate 1 without the possibility of axial movement or rotation.

The holes 2 have a conical shape. The large opening 2a of the holes 2 accessible from the outside of the plate 1 comprise the input for them, while the small opening 2b of the holes 2 opens onto the inside of the plate designed to be applied to the parts of the bone to be assembled. The conical wall 7 of the holes 2 of the inserts 4 is smooth and does not contain any threading before the use of the osteosynthesis plate.

The screws 3 that can be used for fixation of the osteosynthesis plate 1 described above comprise a proximal part or head 8 equipped with a conical threading tapping mechanism 9 having a diameter that increases in the direction of the proximal end of the screws.

These screws are, for example, the type described in the document WO 98/40024. They comprise a distal part 10 provided with a cylindrical threading 11, a proximal part or head 8 equipped with a conical threading tapping mechanism 9, and, preferably, a smooth intermediate section 12 arranged between the distal part 10 and proximal part 8.

The screws are made of any suitable biocompatible material and they can be advantageously of the "cannular" type, i.e. equipped with an axial canal 13 that extends from one end to the other of the screws, for the passage of a pin.

The nominal diameter of the cylindrical threading 11 of the distal part 10 of the screws is less than the diameter of the small opening 2b of the holes 2, so that the distal part of the screws can go through the holes freely during the fixation of the osteosynthesis plate 1 on the bones.

The composite osteosynthesis plate according to the invention allows a tightening of the screws 3 at a certain angulation relative to the axes of the holes 2 of the plate.

Figure 7:
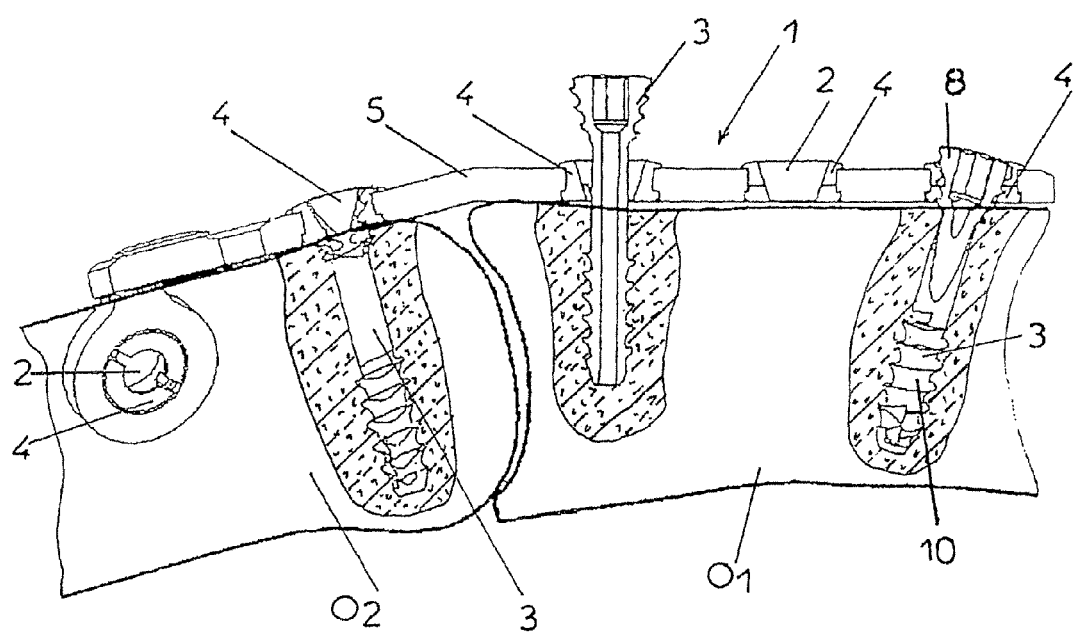
FIG. 7 is an elevation and partial sectional view showing the fixation of an osteosynthesis plate according to the invention for coaptation of bone fragments, two of the fixation screws (right and left) are shown completely tightened into the bone fragments and into the plate, a third screw (in the center) being shown during its implementation.

FIG. 7 shows an example of coaptation of the pieces of the bones O1 and O2 by means of the osteosynthesis device according to the invention.

On the right and left parts of the drawing, the osteosynthesis plate 1 is seen pressed against the bone pieces O1 and O2, by means of two screws 3 completely tightened, whose distal part 10 is tightened into the bone material 14 and whose proximal part 8 is tightened into the inserts 4 of the plate, the screws having different orientations and being locked using the devices described above.

On the central part of the drawing, a screw 3 is shown in the process of being tightened.

As indicated above, the invention makes it possible to obtain a locking of the screws eliminating any possibility of moving back after they are tightened in the bone material. This locking is all the more effective since the conical threaded head tapping mechanism of the screws produces a jamming effect resulting from the conical assembly of the screws and the inserts.

The invention claimed is:

1. An osteosynthesis assembly comprising:
a plate having a plurality of plate openings formed therein, each of said plurality of openings having a peripheral shoulder portion of the plate extended thereinto:
a plurality of one piece inserts fixedly and non-rotationally received in said plurality of openings, each of said plurality of inserts having an inner wall defining a hole, each of said plurality of inserts being formed of a biocompatible material, each of said inserts fixedly and non-rotatably engaging said shoulder of said plate opening; and
a plurality of tapping screws, each screw having a shank and a generally conical, threaded head, threadably secured respectively in the hole of said plurality of inserts, said inner wall of said hole being in self-tapped threaded engagement by a tapping screw,
wherein said inner wall is jammed against said conical threading of each corresponding tapping screw by deformation of the biocompatible material against said conical threading of each screw;
wherein the holes of the inserts have a large opening on an outside side of the plate and a small opening on an inside side of the plate and wherein the holes of the inserts are defined by smooth walls.

2. The osteosynthesis assembly of claim 1, wherein the insert is made from a molded thermoplastic polymer.

3. The osteosynthesis assembly of claim 1, wherein the insert material is made of a machineable material.

4. The osteosynthesis assembly of claim 1, wherein the screws of the plurality of tapping screws have a shank portion that can pass freely through the hole in the insert.

5. The osteosynthesis assembly of claim 1, wherein a base of the conical head of the tapping screws is smaller than the large opening of the hole of the inserts, and wherein the head of the tapping screws is larger than the small opening of the inserts.

6. The osteosynthesis assembly of claim 1, wherein said plate is formed of a metallic material.

7. The osteosynthesis assembly of claim 1, wherein the holes of the inserts have a large opening on an outside of the plate and a small opening on an inside of the plate; wherein the insert is made from a molded thermoplastic polymer; wherein the plate openings include a groove; wherein the insert material is made of a machineable material; and wherein the screws of the plurality of tapping screws have a shank portion that can pass freely through the hole in the insert.

8. The osteosynthesis assembly of claim 1, wherein the holes of the inserts have a large opening on an outside of the plate and a small opening on an inside of the plate; and wherein a base of the conical head of the tapping screws is smaller than the large opening of the hole of the inserts and wherein the head of the screws is larger than the small opening.

9. The osteosynthesis assembly of claim 1, wherein the biocompatible material is adapted to substantially resist biological degradation.

10. An osteosynthesis assembly comprising:
a plate having a plurality of plate openings formed therein, each of said plurality of openings having a peripheral shoulder portion of the plate extended thereinto:
a plurality of one piece inserts fixedly and non-rotationally received in said plurality of openings, each of said plurality of inserts having an inner wall defining a hole, each of said plurality of inserts being formed of a biocompatible material, each of said inserts fixedly and non-rotatably engaging said shoulder of said plate opening; and
a plurality of tapping screws, each screw having a shank and a generally conical, threaded head, threadably secured respectively in the hole of said plurality of inserts, said inner wall of said hole being in self-tapped threaded engagement by a tapping screw,
wherein said inner wall is jammed against said conical threading of each corresponding tapping screw by deformation of the biocompatible material against said conical threading of each screw;
wherein the holes of the inserts have a large opening on an outside of the plate and a small opening on an inside of the plate; wherein the insert is made from a molded thermoplastic polymer; wherein the plate openings include a groove; wherein the insert material is made of a machineable material; and wherein the screws of the plurality of tapping screws have a shank portion that can pass freely through the hole in the insert.

11. The osteosynthesis assembly of claim 10, wherein the holes of the inserts are defined by smooth walls.

12. The osteosynthesis assembly of claim 11, wherein a base of the conical head of the tapping screws is smaller than the large opening of the hole of the inserts, and wherein the head of the tapping screws is larger than the small opening of the inserts.

13. The osteosynthesis assembly of claim 10, wherein the insert material is made of a machineable material.

14. The osteosynthesis assembly of claim 10, wherein the screws of the plurality of tapping screws have a shank portion that can pass freely through the hole in the insert.

15. The osteosynthesis assembly of claim 10, wherein said plate is formed of a metallic material.

16. The osteosynthesis assembly of claim 10, wherein a base of the conical head of the tapping screws is smaller than the large opening of the hole of the inserts and wherein the head of the screws is larger than the small opening.

17. The osteosynthesis assembly of claim 10, wherein the biocompatible material is adapted to substantially resist biological degradation.

18. An osteosynthesis assembly comprising:
a plate having a plurality of plate openings formed therein, each of said plurality of openings having a peripheral shoulder portion of the plate extended thereinto:
a plurality of one piece inserts fixedly and non-rotationally received in said plurality of openings, each of said plurality of inserts having an inner wall defining a hole, each of said plurality of inserts being formed of a biocompatible material, each of said inserts fixedly and non-rotatably engaging said shoulder of said plate opening; and
a plurality of tapping screws, each screw having a shank and a generally conical, threaded head, threadably secured respectively in the hole of said plurality of inserts, said inner wall of said hole being in self-tapped threaded engagement by a tapping screw,
wherein said inner wall is jammed against said conical threading of each corresponding tapping screw by deformation of the biocompatible material against said conical threading of each screw;
wherein the holes of the inserts have a large opening on an outside of the plate and a small opening on an inside of the plate; and wherein a base of the conical head of the tapping screws is smaller than the large opening of the hole of the inserts and wherein the head of the screws is larger than the small opening.

19. The osteosynthesis assembly of claim 18, wherein the holes of the inserts are defined by smooth walls.

20. The osteosynthesis assembly of claim 18, wherein the insert is made from a molded thermoplastic polymer.

21. The osteosynthesis assembly of claim 18, wherein the insert material is made of a machineable material.

22. The osteosynthesis assembly of claim 18, wherein the screws of the plurality of tapping screws have a shank portion that can pass freely through the hole in the insert.

23. The osteosynthesis assembly of claim 18, wherein said plate is formed of a metallic material.

24. The osteosynthesis assembly of claim 18, wherein the insert is made from a molded thermoplastic polymer; wherein the plate openings include a groove; wherein the insert material is made of a machineable material; and wherein the screws of the plurality of tapping screws have a shank portion that can pass freely through the hole in the insert.

25. The osteosynthesis assembly of claim 18, wherein the biocompatible material is adapted to substantially resist biological degradation.

26. An osteosynthesis assembly comprising:
a plate having a plurality of plate openings;
a plurality of one piece inserts, each insert fixedly and non-rotationally engaged with a plate opening, each insert defining a hole having a smooth inner wall;
a plurality of screws, each having a shank and a generally conical, threaded head dimensioned to and made of a material adapted to deform the inner walls of the insert when engaged therewith and jam the screw therein;
wherein the screws are made of a biocompatible material, are cannular, and have shank diameter small enough to pass through the inserts freely; wherein the inner walls of each of the plurality of inserts is at least partially conically shaped and adapted to receive the threads of the screws such that the threads at least partially penetrate the walls; wherein each of the plurality inserts is made from a machineable material; wherein the plurality inserts are made from a high performance thermoplastic polymer; wherein the inserts have a large opening on an outer surface thereof and small opening on an inside surface thereof; and wherein the plate opening defines a peripheral groove and the inserts are made of a material adapted to deformably engage the peripheral groove.

27. The osteosynthesis assembly of claim 26, wherein the inner walls of the one piece inserts are generally conical.

28. The osteosynthesis assembly of claim 26, wherein the plate openings have a peripheral shoulder portion of the plate extending thereinto.

29. The osteosynthesis assembly of claim 26, wherein the inserts are composed of a biocompatible material that is adapted to substantially resist biological degradation.

* * * * *